US00PP27503P3

(12) United States Plant Patent
Cain et al.

(10) Patent No.: US PP27,503 P3
(45) Date of Patent: Dec. 27, 2016

(54) PLUM TREE NAMED 'SUPLUMFORTYSEVEN'

(50) Latin Name: *Prunus salicina*
Varietal Denomination: Suplumfortyseven

(71) Applicant: Sun World International, LLC, Bakersfield, CA (US)

(72) Inventors: David Cain, Bakersfield, CA (US); Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 166 days.

(21) Appl. No.: 14/121,905

(22) Filed: Oct. 31, 2014

(65) Prior Publication Data

US 2016/0128250 P1 May 5, 2016

(51) Int. Cl.
*A01H 5/08* (2006.01)

(52) U.S. Cl.
USPC ..... Plt./184

(58) Field of Classification Search
USPC ..... Plt./184
See application file for complete search history.

*Primary Examiner* — Keith Robinson
(74) *Attorney, Agent, or Firm* — Knobbe, Martens, Olson & Bear, LLP

(57) ABSTRACT

A new and distinct plum tree variety, *Prunus salicina,* cv. 'Suplumfortyseven' is characterized by mid-season ripening fruit having a dark red flesh, nearly black skin, and a semi-free stone. The fruit is medium in sugar and has medium acidity. The fruit of the new variety 'Suplumfortyseven' is also abundant in juice and has a mildly sweet flavor. The new variety ripens before 'Joanna Red' (U.S. Plant Pat. No. 10,385) and harvest is later than for 'Suplumeleven' (U.S. Plant Pat. No. 4,902).

1 Drawing Sheet

Latin name of the genus and species claimed: *Prunus salicina.*

Variety denomination: 'Suplumfortyseven'.

BACKGROUND AND SUMMARY OF THE INVENTION

This invention relates to the discovery and asexual propagation of a new and distinct variety of plum, *Prunus salicina* cv. 'Suplumfortyseven'. The new variety was first originated by hybridization in August 2001 by David Cain and Terry A. Bacon as breeder number '96P024-003-430'.

The new variety 'Suplumfortyseven' is characterized by mid-season ripening fruit having dark-red flesh, nearly black skin, and a semi-free stone. The fruit is medium in sugar and has medium acidity. The fruit of the new variety 'Suplumfortyseven' is also abundant in juice and has a mildly sweet flavor.

The seed parent is '91P-098' (unpatented breeding variety), and the pollen parent is unknown (open-pollenated). The parent varieties were first crossed in February 1996, with the date of first sowing being February 1997, and the date of first flowering being February 1998. The new plum variety 'Suplumfortyseven' was first asexually propagated by Terry Bacon near Wasco, Kern County, Calif. in January 2002 by grafting.

The new variety 'Suplumfortyseven' is distinguished from its seed parent '91P-098' (unpatented breeding variety) in that the fruit of the new variety ripens about 29 days before that of '91P-098'. The fruit of the new variety 'Suplumfortyseven' also has a red flesh color compared to the yellow flesh color of '91P-098'.

The harvest of the new variety 'Suplumfortyseven' starts about 20 days after the harvest of 'Suplumeleven' (U.S. Plant Pat. No. 4,902). The fruit of the new variety 'Suplumfortyseven' has a dark red flesh compared to the slightly pink flesh of the fruit of 'Suplumeleven' (U.S. Plant Pat. No. 4,902). The fruit of the new variety 'Suplumfortyseven' ripens about 11 days before the fruit of 'Joanna Red' (U.S. Plant Pat. No. 10,385), while the fruit of the new variety 'Suplumfortyseven' has nearly black skin compared to the red skin of the fruit of 'Joanna Red' (U.S. Plant Pat. No. 10,385).

The new variety 'Suplumfortyseven' has been shown to maintain its distinguishing characteristics through successive asexual propagations by, for example, grafting.

BRIEF DESCRIPTION OF THE PHOTOGRAPH

The accompanying color photographic illustration FIG. 1 shows typical specimens of the foliage and fruit of the present new plum variety 'Suplumfortyseven'. The illustration shows leaves and fruit taken from a 5 year old plant. The illustration shows the upper and lower surface of the leaves, a view of the fruit as a whole, the stone as a whole, and a sectional view of a fruit divided across its suture plane to show flesh color, pit cavity and the stone remaining in place. The photographic illustration was taken shortly after being picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon the R.H.S. Colour Chart published by The Royal Horticultural Society, London, England, 1986.

The descriptive matter which follows pertains to 8 year old 'Suplumfortyseven' plants, grown in the vicinity of Wasco, Kern County, Calif., during 2014, and is believed to apply to plants of the variety grown under similar conditions of soil and climate elsewhere.

TREE

General: (Measurements taken on an 14 year old tree unless otherwise noted.)

*Size*.—Medium, reaches a height of approximately 3 meters including normal pruning.

*Spread*.—Approximately 3 meters.

*Vigor*.—Medium, growth of about 1.8 m to 2 m in height the first growing season.

*Growth*.—Semi-upright.

*Productivity*.—Productive, fruit set is usually two or more times desired amount for marketable size fruit. Thinning and spacing of fruit is necessary.

*Form*.—Vase formed.

*Bearer*.—Regular.

*Fertility*.—Unknown, should be planted with another plum variety to ensure consistent production.

*Canopy density*.—Medium, pruning is required to open tree vase shape, allowing more sunlight to reach the center of the tree.

*Hardiness*.—Hardy in all fruit growing areas of California. Winter chilling requirement is approximately 650 hours at or below 7.2° C.

*Disease resistance/susceptibility*.—Under close observation in Kern County, California, no particular plant/fruit disease resistance/susceptibility has been observed.

*Insect resistance/susceptibility*.—Under close observation in Kern County, California, no particular plant/fruit insect resistance/susceptibility has been observed.

Trunk: (Measurements at approximately 30 cm above soil line on mature tree).

*Diameter*.—Approximately 14 cm, and varies with soil type, fertility, climatic conditions and cultural practices.

*Texture*.—Medium shaggy, increases with age of tree.

*Trunk color*.—About Dark Greyed-White 156A in exposed areas to about Medium Greyed-Orange 164B in recesses; becomes darker with age.

Branches: (Measurements at approximately 90 cm above soil line.).

*Size*.—Diameter approximately 8 cm.

*Texture*.—Smooth to slightly shaggy, increasing with tree age.

*Color*.—Varying between about Medium Greyed-Green 197D to about Dark Greyed-Green 197B on exposed areas, to about Medium Greyed-Orange 164C in recesses.

*Lenticels*.—Present.

Lenticels:

*Number*.—Medium.

*Density*.—Varies with tree vigor and climatic conditions, about 2/cm$^2$.

*Color*.—About Medium Grey-Brown 199B.

*Size*.—Medium.

*Length*.—3 mm.

*Width*.—2 mm.

Flowering shoots: (Data taken in September at mid-point of current season growth.).

*Size*.—Average diameter approximately 4 mm.

*Color*.—Topside: About Dark Greyed-orange 176A. Underside: About Dark Greyed-Orange 176A with about Medium Green 138B background.

*Internode length*.—Medium; approximately 2 cm. Midway on flowering shoot.

*Flowering shoot lenticels*.—Moderate amount. Color: About Medium Greyed-Orange 164B. Diameter: Approximately 0.5 mm.

*Flowering shoot leaf buds*.—Shape: Broad obovate. Width: Approximately 2 mm. Length: Approximately 2 mm. Color: About Dark Greyed-Orange 166A.

*Flowering shoot flower buds*.—Shape: Ovoid. Width: Approximately 1.2 mm. Length: Approximately 2 mm. Color: About Dark Greyed-Orange 166A. Number of buds per node: 2-4, usually 2.

*Intensity*.—Medium.

*Density of buds*.—Medium.

*Flower bud distribution*.—On spurs and one year old shoots and older wood.

*Ratio of wood (leaf) buds to flowering buds*.—½ on nodes.

*Anthocyanin intensity*.—Strong.

*Spurs length*.—Usually 5 mm.

*Vegetative bud size*.—Length 2 mm, width 1.5 mm.

*Position of vegetative bud in relation to shoot*.—Slightly held out.

FOLIAGE

Leaves: (Data taken in September on fully expanded leaves at mid-point of the current season growth.).

*Size*.—Medium.

*Average length*.—Medium; approximately 85 mm.

*Average width*.—Medium; approximately 43 mm.

*Thickness*.—Medium.

*Color*.—Upper surface: About Dark Green 139A. Lower surface: About Medium Green 139C.

*Form*.—Broad obovate.

*Tip*.—Cuspidate.

*Base*.—V-shaped.

*Margin*.—Crenate.

*Venation*.—Pinately net veined.

*Vein color*.—About Light Green 139D.

*Surface texture*.—Smooth on both the upper and lower sides.

*Leaf blade (ratio of length to width)*.—Medium, about 2:1.

*Shape in the cross section*.—Concave.

*Angle at apex*.—Small.

*Profile*.—Up folded.

*Leaf blade tip*.—Curved downward.

*Angle of tip*.—Acute.

*Undulation of margin*.—Slight.

*Glossiness of upper side*.—Weak.

*Density of pubescence of lower side*.—Absent or very slight.

*Position of nectaries*.—Absent.

Petiole:

*Average length*.—Medium; approximately 9 mm.

*Average diameter*.—Approximately 1.5 mm.

*Color*.—About Light Green 139D.

*Thickness*.—Medium, approximately 1.1 mm.

Stipules:
*Number/leaf bud.*—Approximately 0-2 per leaf bud when present.
*Typical length.*—Approximately 8 mm.
*Color.*—About Medium Yellow-Green 147C.
*Persistence.*—Falls off.
*Width.*—Approximately 2 mm.
Leaf glands:
*Average number.*—Approximately 0.

FLOWERS

General:
*Flower blooming period.*—First bloom: Approximately March 2. Full bloom: Approximately March 6.
*Location of first bloom.*—Top of tree.
*Location of full bloom.*—Mid-section of the canopy.
*Time of bloom.*—Medium.
*Duration of bloom.*—Medium; approximately 12 days.
*Diameter of fully opened flower.*—Medium, approximately 7 mm.
*Flower aroma.*—Slight.
*Shape.*—Rosaceous.
Pedicel:
*Length.*—Medium; approximately 12 mm.
*Diameter.*—Slender; approximately 1.5 mm.
*Color.*—About Medium Yellow-Green 144B.
*Pubescence.*—Absent.
Petals:
*Number.*—5.
*Arrangement.*—Overlapping.
*Length.*—Approximately 9 mm.
*Diameter.*—Approximately 6 mm.
*Shape.*—Obovate.
*Apex shape.*—Rounded.
*Base shape.*—Narrows at point of attachment.
*Color of inner and outer surface.*—About white 155D.
*Surface texture.*—Smooth, on both the upper and lower sides.
*Margins.*—Undulating.
*Frequency of flowers with double petals.*—None.
*Size.*—Medium.
*Claw length.*—Medium, approximately 1 mm.
*Margin waviness.*—Medium.
*Base angle.*—Narrow.
*Division of upper margin.*—Entire.
*Pubescence of inner surface.*—Absent.
*Pubescence of outer surface.*—Absent.
Sepals:
*Number.*—5.
*Length.*—Approximately 3 mm.
*Diameter.*—Approximately 3 mm.
*Shape.*—Triangular.
*Color.*—About Medium Yellow-Green 144A.
*Surface texture.*—Smooth, on both the upper and lower sides.
*Margins.*—Entire.
*Positioning.*—Adpressed to petals.
*Pubescence of inner surface.*—Absent.
*Pubescence of outer surface.*—Absent.
*Frequency of flowers with double sepals.*—None.
Stamens:
*Number.*—Usually 25-30.
*Average length.*—About 1-10 mm.
*Filament color.*—About White 155D.
*Anther color.*—About Dark Greyed-Yellow 162A.
*Flower pollen color.*—About Dark Greyed-Yellow 162A when dried.
*Position.*—Perigynous.
*Amount of pollen.*—Medium.
Pistil:
*Number.*—Usually one, occasionally 2.
*Average length.*—Approximately 6-9 mm.
*Ovary diameter.*—Approximately 1 mm.
*Pubescence.*—None.
*Stigma extension in comparison to anthers.*—Usually below.
*Style frequency of supplementary pistils.*—Few.
Flower-buds:
*Positioning.*—Slightly held out.
*Pubescence.*—Absent.
Receptacle:
*Depth.*—Medium.
*Size.*—Approximately 4 mm long by 4 mm wide.
*Pubescence of inner surface.*—Absent.
*Pubescence of outer surface.*—Absent.
Ovary:
*Pubescence.*—Absent.
*Diameter.*—Approximately 1 mm.
*Color.*—About Medium Green 137D.
Style:
*Pubescence (of base).*—Absent.

FRUIT

General: (Description taken near Wasco, Kern County, Calif. on July 24).
*Date of first pick.*—Approximately July 20.
*Date of last pick.*—Approximately July 30.
*Maturity when described.*—Firm-mature.
*Season ripening.*—Medium.
*Position of maximum diameter.*—Middle.
*Symmetry about the suture.*—Symmetric.
*Shape of base.*—Flat.
Size:
*Length (stem end to apex).*—Approximately 65 mm.
*Diameter in line with suture plane.*—Approximately 67 mm.
*Diameter perpendicular to suture plane.*—Approximately 67 mm.
*Average weight.*—Approximately 165 gm.
Form:
*Viewed from apex.*—Rounded.
*Viewed from side, facing suture.*—Rounded, slightly elongated.
*Viewed from side, perpendicular to suture.*—Rounded, slightly elongated.
Apex shape: Rounded.
Fruit stem cavity:
*Shape.*—Elongated in suture plane.
*Depth.*—Medium; Approximately 0.8 cm.
*Breadth.*—Approximately 1 cm.
*Width.*—Narrow, approximately 5 mm.
Fruit stem:
*Length.*—Medium; approximately 8 mm.
*Diameter.*—Approximately 3 mm.
*Color.*—About Light-Yellow-Green 147D.
*Adherence to stone.*—Weak.
Fruit skin:
*Thickness.*—Medium.
*Adherence to flesh.*—Weak.
*Surface texture.*—Smooth.
*Pubescence.*—None.
*Bloom.*—Medium-heavy.

*Ground color*.—About Medium Red 42B when visible.
*Overcolor*.—About Dark Greyed-Purple 187A to about Dark Black 202A.
*Relative area of overcolor*.—100%.
*Pattern of overcolor*.—Mostly solid in appearance, with small lenticels slightly visible.
*Taste*.—Mildly tart.
*Reticulation*.—Slight.
*Roughness*.—Absent.
*Tenacity*.—Tenacious to flesh.
*Tendency to crack*.—None in wet season.

Flesh:
*Ripens*.—Evenly.
*Texture*.—Fine.
*Fibers*.—Few.
*Flavor*.—Mildly sweet.
*Brix*.—Approximately 17°.
*Juice*.—Abundant to moderate.
*Aroma*.—Slight fruity aroma.
*Color*.—About Medium Red 46C.
*Anthocyanin color around stone*.—About Medium Red 46C.
*Anthocyanin color of flesh*.—Strongly expressed throughout evenly.
*Acidity*.—Low.
*Sugar content*.—Medium.
*Eating quality*.—Good.
*Stone/flesh ratio*.—Small, about 1/30.
*Firmness*.—Medium.

Pit cavity size:
*Length*.—Approximately 23 mm.
*Diameter perpendicular to suture plane*.—Approximately 18 mm.
*Diameter in line with suture*.—Approximately 10 mm.
*Color*.—About Medium Red 46C.

Fruit use: Fresh market.

Fruit shipping and keeping quality: Good.

Stone:
*Stone freeness*.—Semi-free over the entire surface.
*Degree of adherence to flesh*.—Medium.
*Stone size*.—Size: Medium. Size compared to Fruit: Small. Length: Medium, approximately 23 mm. Diameter in line with suture plan: Approximately 18 mm. Diameter perpendicular to suture plane: Approximately 10 mm. Width of Stalk End: Medium, Approximately 8 mm. Angle of Stalk end: Right angle. Hilum: Oval.
*Stone form*.—Viewed from side: Oval with flat base. Viewed from ventral end: Flattened. Viewed from Stem end: Narrowly oval.
*Stone shape*.—Base shape: Nearly straight. Apex shape: Rounded with small point.
*Hilum*.—Oval.
*Stone surface*.—Slightly rough with irregular shallow furrows.
*Stone halves*.—Nearly symmetrical.
*Stone ridges*.—Rough, rounded, continuous.
*Stone outgrowing keel*.—Well-developed.
*Stone tendency to split*.—Almost none.
*Stone color*.—About Medium Greyed-Orange 166D.
*Position of maximum*.—Middle.
*Sides*.—Nearly equal.
*Pits*.—Angular.
*Ventrical edge*.—Narrow.
*Dorsal edge*.—Narrow continuous.

Lenticels:
*Number*.—Approximately 45 lenticels/cm2.
*Size*.—Approximately 0.5 mm.

What is claimed is:

1. A new and distinct plum tree as herein described and illustrated.

* * * * *

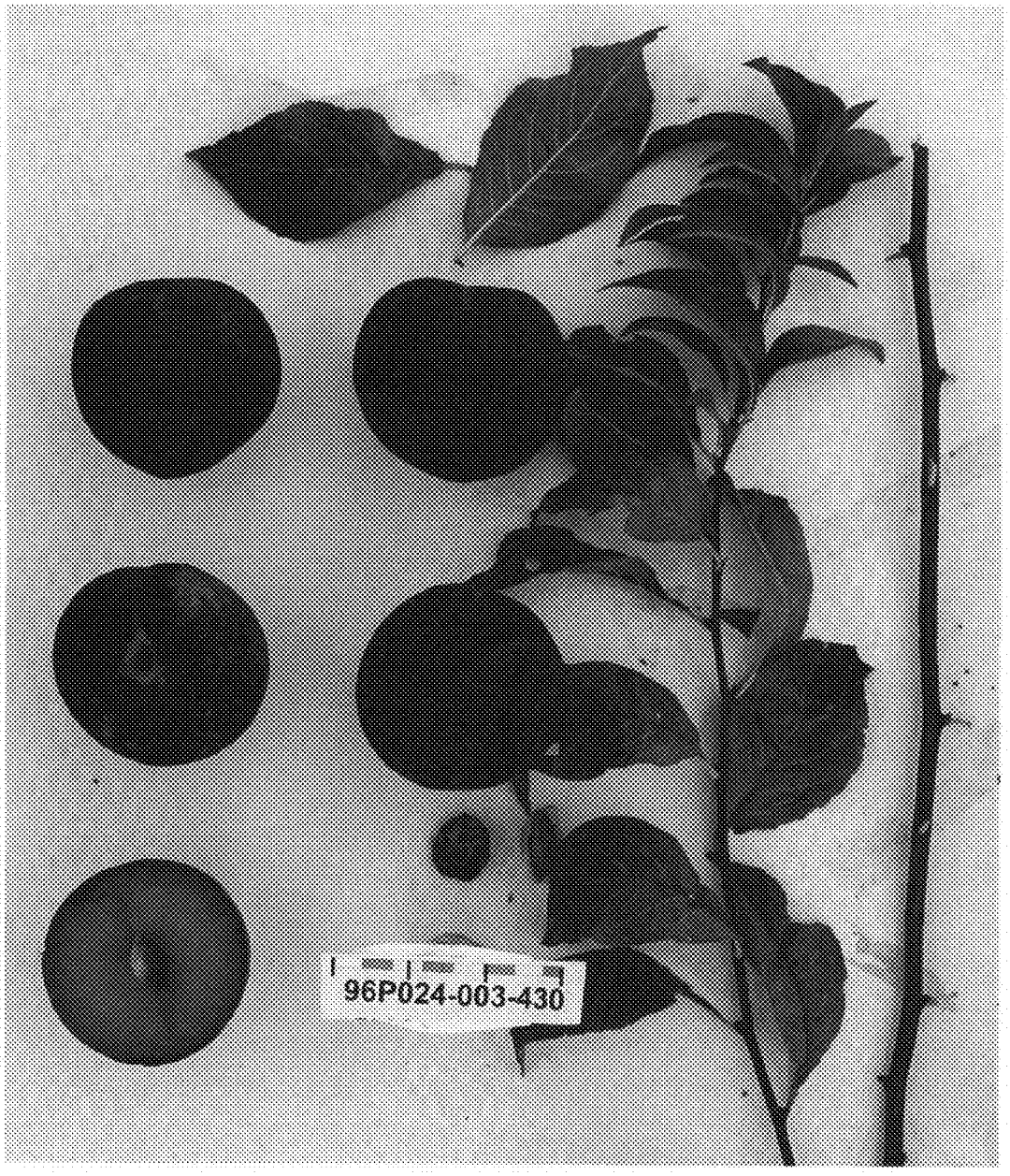
96P024-003-430